United States Patent [19]
Sayama et al.

[11] Patent Number: 5,759,181
[45] Date of Patent: Jun. 2, 1998

[54] DISPOSABLE DIAPER

[75] Inventors: Yasushi Sayama; Yoshitaka Mishima, both of Kagawa-ken, Japan

[73] Assignee: Uni-Charm Corporation, Ehime-ken, Japan

[21] Appl. No.: 730,259

[22] Filed: Oct. 15, 1996

[30] Foreign Application Priority Data

Oct. 13, 1995 [JP] Japan .................. 7-265510

[51] Int. Cl.⁶ .................................................. A61F 13/15
[52] U.S. Cl. .................................................. 604/391
[58] Field of Search ............................ 604/389–391

[56] References Cited

U.S. PATENT DOCUMENTS

| | | | |
|---|---|---|---|
| 4,963,140 | 10/1990 | Robertson et al. | 604/391 |
| 5,071,414 | 12/1991 | Elliott . | |
| 5,176,671 | 1/1993 | Roessler et al. | 604/391 |
| 5,605,735 | 2/1997 | Zehner et al. | 604/391 |

FOREIGN PATENT DOCUMENTS

| | | |
|---|---|---|
| 0 324 578 | 1/1989 | European Pat. Off. . |
| 0 374 730 | 6/1990 | European Pat. Off. . |
| 0 595 047 | 9/1993 | European Pat. Off. . |
| 6-61227 | 8/1994 | Japan . |

*Primary Examiner*—Robert A. Clarke
*Attorney, Agent, or Firm*—Lowe Hauptman Gopstein & Berner

[57] ABSTRACT

A disposable diaper has front and rear waist regions adapted to be separably connected to each other by surface fasteners. Each surface fastener has a hooked fastener component and a looped fastener component operatively associated with the hooked fastener component. At least a pair of wings extending outward from transversely opposite sides of the rear waist region have their outer surfaces made of nonwoven fabric with which the component can be interlocked, enabling the used disposable diaper to be reliably rolled-up for disposal.

4 Claims, 2 Drawing Sheets

DISPOSABLE DIAPER

BACKGROUND OF THE INVENTION

The present invention relates to a disposable diaper having front waist and rear waist regions adapted to be separably connected to each other in its actual use.

There is disclosed in Japanese Laid-Open Utility Model Application No. Hei6-61227 a disposable diaper having front and rear waist regions separably connected to each other by a pair of surface fasteners each comprising a hooked fastener component and a looped fastener component. In this diaper, a pair of tape strips extend outward from transversely opposite side edges of the rear waist region, respectively. Each of the tape strips carries on its inner surface the hooked fastener component, an adhesive zone and a cover zone to protect the adhesive zone arranged in this order starting from the longitudinally inner end of the tape strip. For disposal, the used diaper is rolled up and the adhesive zones on the respective tape strips get interlocked with the diaper at appropriate locations thereof to keep it in a rolled-up state.

With the diaper being worn on the baby's body, the hooked fastener components on the respective tape strips are interlocked with the associated looped fastener components, and the adhesive zones on the respective tape strips are covered with the folded cover zones on the same tape strips so as to form tabs. The adhesive zones must have sufficient lengths to assure that the used diaper is reliably kept in its rolled-up state and the tabs inevitably have correspondingly long dimensions. Consequently, there is an apprehension that the baby wearing such a diaper may easily hold these long tabs and take of f the diaper by him- or herself.

SUMMARY OF THE INVENTION

Accordingly, it is a principal object of the invention to provide a disposable diaper adapted to be reliably kept in its rolled-up state for disposal after its use and being free from the above-mentioned apprehension.

The object set forth above is achieved, according to the invention, by a disposable diaper comprising a liquid-permeable topsheet, a liquid-impermeable backsheet and a liquid-absorbent core disposed between these two sheets, respective pairs of front and rear wings extending outward from transversely opposite sides of front and rear waist regions of the diaper, one of the pairs carrying a pair of hooked fastener components and the other pair carrying a pair of looped fastener components adapted to be separably interlocked with the hooked fastener components, the diaper being characterized by that the hooked fastener components are bonded to inner surfaces of the front or rear wings and outer surfaces of the wings are made of nonwoven fabric with which the hooked fastener components are peelably interlocked.

DETAILED DESCRIPTION OF THE PREFERRED EMBODIMENT

Figure 1:
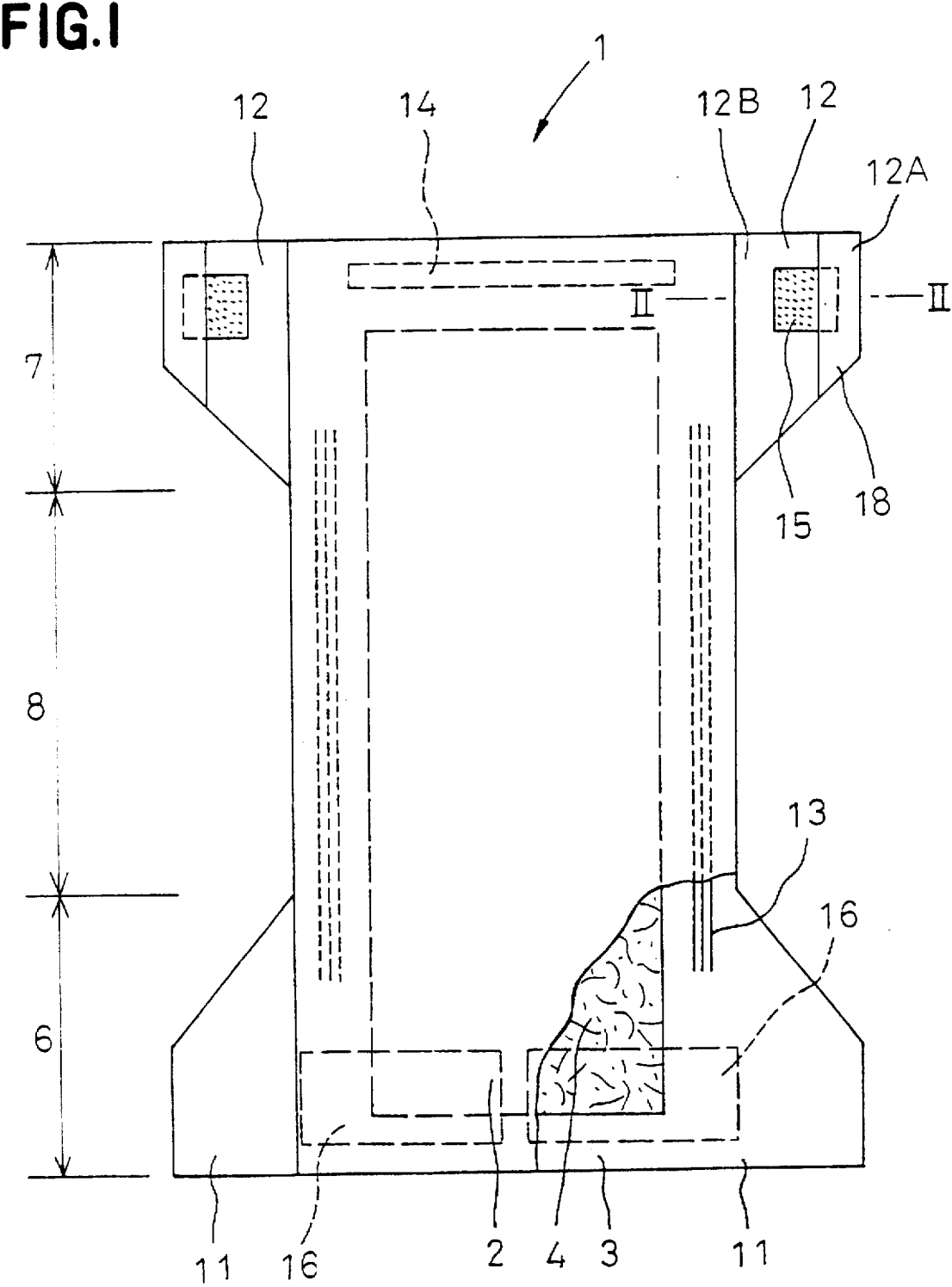
FIG. 1 is a plan view showing an embodiment of the inventive diaper as partially broken away.

A diaper 1 shown by FIG. 1 in a plan view as partially broken away comprises a liquid-permeable topsheet 2, a liquid-impermeable backsheet 3 and a liquid-absorbent core 4 disposed between these two sheets 2, 3. The diaper has a front waist region 6, a rear waist region 7 and a crotch region 8 extending between these two regions 6, 7. The front and rear waist regions 6, 7 are provided along their transversely opposite sides with front wings 11 and rear wings 12, respectively. The topsheet 2 and backsheet 3 are put one upon another over their portions extending outward beyond a peripheral edge of the core 4 and inner surfaces of these portions are water-tightly bonded together. The crotch region 8 is provided adjacent its transversely opposite side edges with elastic members 13 adapted to surround the wearer's legs and the rear waist region 7 is provided adjacent its longitudinal end with an elastic member 14 extending along the waist line. These members 13, 14 are disposed between the topsheet 2 and backsheet 3 and secured in an elastically contractible condition to the inner surface of at least one of these two sheets 2, 3.

A hooked fastener component 15 having a plurality of hook elements, one component of a surface/mechanical fastener known under the trademark of Velcro, is anchored to the inner surface of each rear wing 12 and a part of this hooked fastener component 15 extending aside to an outer side edge 12A of the wing 12 has its inner surface covered with a protective sheet 18. A looped fastener component 16 having a plurality of loop elements, the other component of the surface/mechanical fastener, is anchored to the outer surface of each front wing 11 so as to extend transversely thereof.

Figure 2:
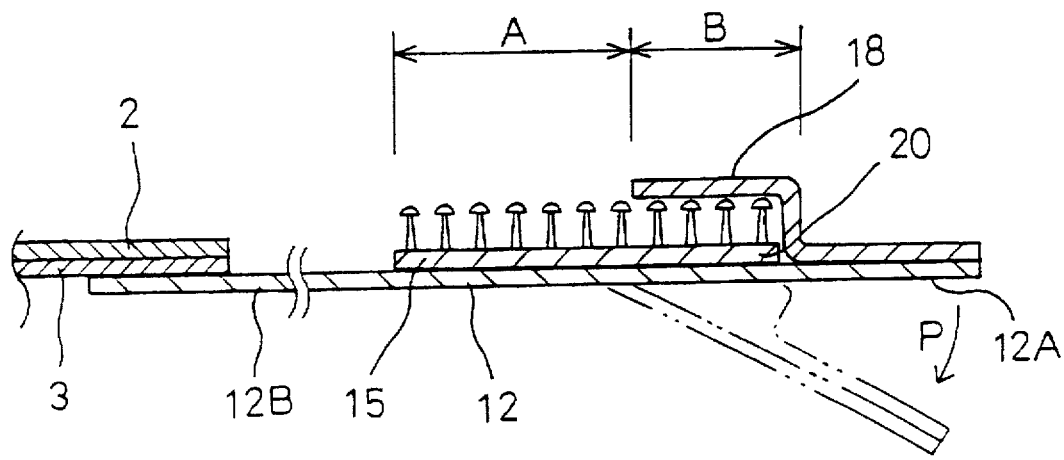
FIG. 2 is a sectional view taken along a line II—II in FIG. 1.

FIG. 2 is a sectional view taken along a line II—II in FIG. 1. As shown, an inner side edge 12B of each rear wing 12 is joined to a side edge of the outer surface of the backsheet 3. An exposed portion of the hooked fastener component 15 defined by a width A is peelably interlocked with the associated looped fastener component 16 while the portion defined by a width B covered with the protective sheet 18 does not participate in fastening. The hooked fastener component 15 once interlocked with the associated looped fastener component 16 is pulled in the direction as indicated by an arrow P with the outer side edge 12A of the rear wing 12 being held by the user's fingers so that the portion defined by the width A may be peeled off from the rear wing 12 starting from its right side, as indicated by the imaginary lines. In this state, so-called peeling force is practically ineffective between the rear wing 12 and an outer side edge 20 of the hooked fastener component 15, so the outer side edge 20 is not peeled off from the rear wing 12.

Figure 3:
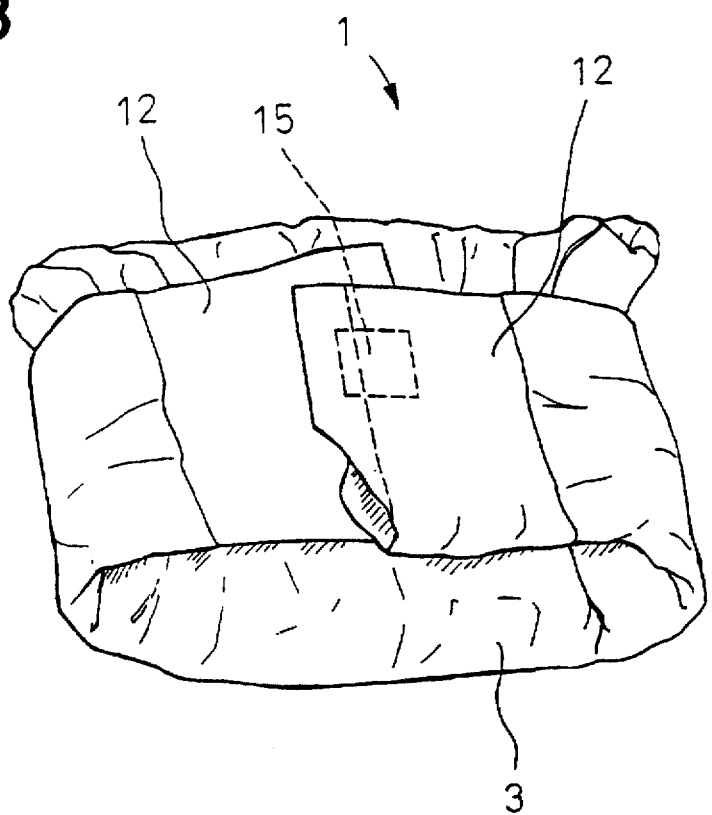
FIG. 3 is a perspective view showing the diaper as rolled up.

FIG. 3 is a perspective view showing the used diaper 1 as rolled up for disposal. The diaper 1 is rolled-up starting from the front waist region 6 toward the rear waist region 7 with the topsheet 2 inside, and then the rear wings 12 are folded inward so that the hooked fastener component 15 associated with one of the rear wings 12 may be interlocked with the outer surface of the other rear wing 12. With the diaper 1 according to the illustrated embodiment, such fastening of the member 15 is facilitated by using nonwoven fabric such as spun lace nonwoven fabric or spun bond nonwoven fabric which is bulky and relatively fluffy, or composite fiber nonwoven fabric comprising crimped fibers entangled together and thereby forming a plurality of fine loops, to make at least the rear wings 12 or their outer surfaces. If the topsheet 2 and/or the backsheet 3 are made of such nonwoven fabric, the rear waist region 7 of these sheet 2 and/or sheet 3 may be transversely extended so as to form the respective rear wings 12. If the rear wings 12 are provided with, instead of the hocked fastener components 15 as illustrated, so-called tape fasteners comprising tape strips laterally extending from outer ends of the respective rear wings 12 and the hooked fastener components 15 are respectively bonded to inner surfaces of the tape strips. the tape strips or outer surfaces thereof may be also made of the nonwoven fabric so that the hooked fastener components 15 can be interlocked with such nonwoven fabric.

To implement the invention. the appropriate materials commonly used in the concerned field of technique may be used for the topsheet 2 and the backsheet 3. In the illustrated embodiment. nonwoven fabric or plastic film which is less rigid than the hooked fastener component 15 and agreeable to the touch is used as material for the protective sheet 18. Bonding of the respective components or members may be achieved by use of adhesive. e.g.. of hot melt type or by utilizing a heat-seal technique so far as the components or members to be bonded are of heat-sealable nature. It should be noted that no specific manner of bonding is illustrated.

With the inventive diaper. the front and rear waist regions are separably connected to each other by the surface fastener comprising the hooked fastener component and the looped fastener component wherein the diaper wings are made of nonwoven fabric with which the hooked fastener component can be interlocked so that. after the used diaper has been rolled-up for disposal. the hooked fastener component can be reliably interlocked with the nonwoven fabric to keep the used diaper in the rolled-up state. The diaper of such arrangement requires no adhesive fastening means to retain the diaper in the rolled-up state and allows a tab used to peel off the hooked fastener component from the rear wing to be formed in a small size. so that as it will be difficult for the baby to hold the tab.

What is claimed is:

1. A disposable diaper comprising:

a liquid-permeable topsheet;

a liquid-impermeable backsheet;

a liquid-absorbent core disposed between said topsheet and said backsheet;

respective pairs of front and rear wings extending outward from transversely opposite sides of front and rear waist regions of said diaper;

said pair of rear wings carrying a pair of hooked fastener components;

said pair of front wings carrying a pair of looped fastener components adapted to be separably interlocked with said hooked fastener components;

wherein each said hooked component is anchored to an inner surface of each said rear wing;

wherein each said hooked fastener component extending aside to an outer side edge of each said rear wing has an inner surface of each said hooked fastener component covered with a protective sheet; and wherein outer surfaces of said rear wings are made of nonwoven fabric with which said hooked fastener components are peelably interlocked.

2. A disposable diaper according to claim 1. wherein said protective sheet is made of nonwoven fabric or plastic film which is less rigid than said hooked fastener component.

3. A disposable diaper according to claim 1. wherein the pair of wings having said hooked fastener components anchored thereto comprise tape strips extending outward from transversely opposite side edges of said wings and said hooked fastener components are anchored to inner surfaces of said tape strips and wherein said pair of wings as well as said tape strips have their outer surfaces made of said nonwoven fabric.

4. A disposable diaper according to claim 1. wherein said hooked fastener components have a plurality of hook elements. said looped fastener components having a plurality of loop elements.

\* \* \* \* \*